(12) United States Patent
Toeppen-Sprigg (10) Patent No.: US 6,544,172 B2
(45) Date of Patent: Apr. 8, 2003

(54) METHODS FOR EVALUATING INDIVIDUALS CAPACITY AND ESTABLISHMENT OF REQUIREMENTS FOR A JOB

(75) Inventor: Barbara Ruth Toeppen-Sprigg, Canton, OH (US)

(73) Assignee: The Goodyear Tire & Rubber Company, Akron, OH (US)

(*) Notice: Subject to any disclaimer, the term of this patent is extended or adjusted under 35 U.S.C. 154(b) by 87 days.

(21) Appl. No.: 09/850,811

(22) Filed: May 8, 2001

(65) Prior Publication Data

US 2002/0188178 A1 Dec. 12, 2002

(51) Int. Cl.7 .............................. A61B 5/00; A61B 5/08
(52) U.S. Cl. ...................... 600/300; 600/529; 600/531
(58) Field of Search ................................. 600/300–301, 600/529–538; 128/920, 897–898; 482/8, 148, 901

(56) References Cited

U.S. PATENT DOCUMENTS 5,680,866 A * 10/1997 Kangas et al. ............... 600/484

* cited by examiner

*Primary Examiner*—Max F. Hindenburg
*Assistant Examiner*—Michael Astorino
(74) *Attorney, Agent, or Firm*—David L. King (57) ABSTRACT

A practical and improved method for evaluating the cardiopulmonary demands of work processes or tasks is disclosed. The methodology uses three different modes of analysis—measurement of ventilation, continuous heart rate monitoring, and aerobic capacity testing. An individual (2) while wearing a ventilation device (10) and a heart monitor (20) is tested for oxygen used, the work heart rate and the energy required is kilocalories for the activities measured. The data is recorded and compiled establishing the individuals response. The testing permits work to be analyzed and matches individuals capacity to perform the work in a new and cost effective way.

9 Claims, 8 Drawing Sheets

| Test Individual | METS | Ave HR | HRRU | Working HRRU | O2 Cons | Kcal/ Min | Body Mass Index | Level |
|---|---|---|---|---|---|---|---|---|
| 1 | 6 | 105 | 105 | 35.8 | 0.8247 | 3.65 | 33.4 | Moderate |
| 2 | 9.4 | 100 | 25.2 | 27.9 | 1.0113 | 4.5 | 24.7 | Moderate |
| 3 | 10.9 | 104 | 25.2 | 27 | 0.7929 | 3.49 | 30.3 | Moderate |
| 4 | 7.4 | 103 | 29.4 | 33.3 | | | 24.2 | Moderate |
| 5 | 10 | 90 | 18.4 | 18.4 | | | 29 | Light/ Moderate |

| Criteria | O2 Used | Heart Rate | Kcal/Min |
|---|---|---|---|
| Light | <0.5 | <90 | <2.5 |
| Moderate | 0.5 – 1.0 | 90 – 100 | 2.5 – 5.0 |
| Heavy | 1.0 – 1.5 | 110 – 130 | 5.0 – 7.5 |
| Very Heavy | >1.5 | 130 – 150 | 7.5 – 10 |

FIGURE 3

Aerobic Work Requirements Data Sheet

Name: _______________________________
Time: __________
Date: __________
Job: _______________________________
Length of time in this job: _______________________________
Age: __________
Sex: ☐ Male  ☐ Female Medical History:

The reasons to ask the following questions is to determine if it is safe for you to participate in the testing, and to identify any factors that might affect the results Have you ever had surgery?        ☐ No  If yes, what type and when?
_______________________
Have you ever had a back injury?      ☐ No  If yes, when?
Have you ever had a shoulder injury?  ☐ No  If yes, when?
Have you ever had a heart problem?    ☐ No  If yes, describe it.
Do you currently have chest pain (unstable angina) ☐ No  If yes, describe it Do you take any prescribed medication? ☐ No If yes, list names
How much caffeine (coffee, tea, soft drinks, etc) do you drink a day?
☐     None
☐     One cup
☐     Two cups
☐     Three cups
☐     More than three cups Do you take any over the counter medications? ☐ No    If yes, list:

Do you take any herbal remedies or supplements? ☐ No  If yes, list:

Do you smoke or chew tobacco? ☐ No

Testing:

Weight, including any tools carried and in safety shoes:________ lbs ________kg
Height: __________ inches __________ cm
Blood pressure, seated __________
Resting pulse __________
Results of spirometry __________

Criteria to proceed:
☐     No history of back or shoulder surgery or prolonged absence due to back
☐     No history of cardiac problems
☐     No history of beta blockers
☐     No history of caffeine > two cups, OTC containing caffeine, epinephrine or decongestants, herbal remedies containing ephedra (ephedrine, ma huang)
☐     Normal spirometry See step test protocol for process of testing.

Aerobic capacity ________ METS  ____________max $O_2$
Watch Number:______ File Number: ______ Time of monitor start __________
Evaluator: _______________________________ Certification _______________

FIGURE 4

Protocol for Determining the Aerobic Requirements of Jobs:

1. With the assistance of individuals performing the jobs in question, identify the primary types of activity required in the job. Many jobs have more than one major activity that the individuals rotate between. Each significant section of the job should be sampled, and identified on the "Energy Expenditure Time Study" sheet as a task. Estimates of the amount of time per shift spent in each task should be entered on the sheet under the "time" column in minutes per shift. The spreadsheet will calculate the kcal/shift and totals.
2. After the individual being tested has had their aerobic capacity test and been fitted with the heart monitor, sample each major section of the job for 20 minutes. Be careful to indicate the time of each ventilatory test on the spreadsheet so it can be correlated with the heart rate monitor tracing.
3. Four individuals should be tested for each job.
4. Data for each individual should be entered in the "Worksheet for Energy Expenditure". One worksheet is used for each job.
5. On the criteria table for each job, circle the average result for $O_2$, average work heart rate, and METS to evaluate for consistency. Average heart rate reserve utilization should be less than 30% for validity.

Table:

| Criteria | $O_2$ used | Work Heart Rate Average | Kcal/min | METS Required |
|---|---|---|---|---|
| Light | <0.5 L/min | <90 | <2.5 Kcal | |
| Light/moderate | 0.5 – 0.75 | 90 – 100 | 2.5 – 3.75 | |
| Moderate | 0.75 – 1.0 | 100 – 110 | 3.75 – 5.0 | |
| Moderate/heavy | 1.0 – 1.25 | 110 – 120 | 5.0 – 6.25 | |
| Heavy | 1.25 – 1.5 | 120 – 130 | 6.25 – 7.5 | |
| Very Heavy | > 1.5 | 130 – 150 | 7.5 - 10 | |

Energy Expenditure Time Study

Date: ___________
Job: ___________
Associate: ___________

| Workstation Timing | | Mean Energy Expenditure | | | | | |
|---|---|---|---|---|---|---|---|
| | | Time | | Gross | | Net | |
| # | Task / Operations performed by the worker | Min | Ventilation in L/min | kcal/min | kcal/shift | kcal/min | kcal/shift | Notes |
| | | | | | | | | |
| | | | | | | | | |
| | | | | | | | | |
| | | | | | | | | |
| | | | | | | | | |
| TOTAL | | | | | | | | |

METHODS FOR EVALUATING INDIVIDUALS CAPACITY AND ESTABLISHMENT OF REQUIREMENTS FOR A JOB

FIELD OF THE INVENTION

This invention is related to any job requiring human labor. More specifically this invention enables accurate evaluation of the cardiopulmonary demands of a job to be used in both job modification and in job placement.

BACKGROUND OF THE INVENTION

Historically, the match of individual work to specific jobs was based on a variety of selection processes. In early America for example, slaves were usually more highly valued if they were young, fit and fine physical specimens. The buyers of such workers paid a premium for individuals with the best combination of the attributes. This selection process, while in today's standards, seems cruel for societal reasons, nevertheless recognized the value of such individuals because the long hours of hard and physically demanding work required only truly fit individuals who could perform such demanding work.

As America's society was in its early beginning, farms were a large source of laborers. These farmers and cattlemen were accustomed to long hours, hard work and bodies conditioned to such labor as a result of such demanding physical requirements of their lifestyle. In the 1900's, the supply of young farmers and the like coming to modem factories was large and abundant.

Today's world of more automated modem facilities and a more sedentary nature of a large portion of the work force make the modem worker more valuable for their ability to run complex machinery and direct work through computer-controlled monitors. It is their ability to be well-educated, skilled workers which is most highly rewarded.

These well-trained and educated employees are valuable and any loss of work due to injuries is even more devastating because such individuals are so productive. In recent years the productivity of workers has year after year increased by one or two percent.

The improved productivity has come about by automating equipment and improving material handling equipment, and redesigning the overall workplace.

While all of these improvements have been beneficial to the economy of the countries employing such advances, it is clear that the skilled and trained workers have an ever-increasing value to the success of the enterprise. Worker absenteeism due to injury is very costly, harmful to the individual and generally a situation that needs to be avoided where possible. The risk of injury to workers can come from a number of sources many of which involve the design of the work, the equipment or the overall work station. Engineers routinely look at these factors and try to design more user-friendly environments to reduce work related injuries.

The individual users are preselected and hired based on the employer's perception that they are qualified being both mentally and physically capable of performing work. Job applicants have been required to take physical exams, undergo cursory medical tests, and checked for previous work history prior to being hired. This practice has gone on for years. It has been a process of hiring based on the employer's knowledge of the work he needs done and his experience with other workers that enables him to predict who might be qualified for a certain task. The process of selecting employees who have a high likelihood of being injury free is often times purely subjective. The science of actually knowing what the employer is asking an employee to do is similarly somewhat subjective and relies on past experience.

Gradually, changes have occurred in this process. Recent legislation has tied employment decisions more closely to essential job requirements, and testing against those job requirements is considered valid.

For the most part, workers know they will be asked to perform tasks and that such tasks will be performed over a workday commonly referred to as a shift. Shifts are typically eight to twelve hours and in some cases longer if overtime is requested.

When one asks an employer how much energy is anticipated to be consumed in terms of calories burned per shift or what the total work energy expenditure of the task is that employer is always at a loss for words and yet that is the very nature of a job. Alternatively ask a worker what his working heart rate is during varying periods of exertion or how much air volume he consumes during an eight-hour shift and he too will look puzzled and confused as to the relevancy of such questions.

In this invention, the inventor has determined new and useful ways to evaluate the demands of the job for energy expenditure and cardiorespiratory reserve. Used in conjunction with musculoskeletal demand analysis, job requirements can be set to inform management and prospective employees in ways that allow appropriate and directed testing prior to job initiation.

These measurements are important as they lead to an assessment of endurance and the onset of fatigue. The individual having a known endurance level is less likely to have an injury occur if he or she operates within a work level consistent with his or her capabilities. It is well understood where an individual asks his or her body to perform beyond their capabilities that injury is more likely. When the fatigue or exhaustion factor is introduced or when one exceeds his endurance level mistakes both mental or physical are more likely.

It is in the interest of both the worker and the employer to know in objective terms what is the risk a worker should be allowed to subject his or herself to based on the job requirements and the individual's capabilities. The present invention provides an improved method to quantify an individual's energy abilities and cardiac reserve in a cost efficient and practical way. The method further permits equipment and work process involved in performing a task or activity to be quantified in a way that reflects the capabilities of the individual. The combination of these methods permits workers and capabilities to be matched to the job requirements in a more objective fashion than prior art techniques.

SUMMARY OF THE INVENTION

A practical and improved method for evaluating the cardiopulmonary demands of work processes or tasks is disclosed. The methodology uses three different modes of analysis—measurement of ventilation, continuous heart rate monitoring, and aerobic capacity testing. By comparison of the results of the three modes, a recommendation can be made as to the level of aerobic capacity required of new job entrants to maximize their ability to perform the job safely. While the modes used are well established in the areas of work physiology, they have not been combined in this practical way to increase validity of the testing in the actual work environment rather than in physiology laboratories. There are software programs that can estimate energy expenditure based on weights and repetition, but they have limited applicability in complex manufacturing tasks.

The first requirement is to understand the pattern and timing of the work, so a decision can be made as to the tasks to be studied. Some jobs have essentially one activity that is done throughout the shift, while others have several in a job rotation. Each major segment is studied while a worker wears an energy expenditure meter, a small mask attached to a microprocessor. This unit measures the air passing in and out of the mouth and nose during a defined period of time. The result is adjusted for the sex, age, height and weight of the tested individual, and reported as liters of air per minute as well as kilocalories of energy used. By previously established formulas, the amount of oxygen required, (which comprises roughly 21% of ambient air) can be calculated.

At the same time, the individual wears a continuous heart rate monitor. When the information from the monitor is transferred to a computer program, several items are calculated which reflect the way the heart has responded to the energy required. The heart rate reserve utilization during the time studied with the ventilation monitor is another physiologic response reflecting how hard this individual was working during that period selected. Because many medications, herbal preparations, caffeine, and tobacco affect the heart rate response, a medical history is taken prior to the testing to identify any confounding factors.

The third comparison made is to the measured aerobic capacity of the individual. The more fit a person is, the more effective their heart is at producing a large volume of blood with each beat. This means that the heart does not have to beat as rapidly to perform a set amount of work, and a lower heart rate results. This person will fatigue less rapidly than a person whose heart has to beat more rapidly to get the work done.

By comparing the results of the oxygen and caloric consumption to the heart rate reserve utilization and the aerobic capacity of individuals in the job, the experienced evaluator can look for consistency and set a level of aerobic capacity for new job entrants that will increase the likelihood of success and productivity.

BRIEF DESCRIPTION OF THE DRAWINGS

The invention will be described by way of example and with reference to the accompanying drawings in which:

FIG. 4 is Sample Form showing the data compiled for an individual.

FIG. 5 is an exemplary Protocol for Determining the Aerobic Requirements of Jobs.

DETAILED DESCRIPTION OF THE INVENTION

The following invention studies the effects of job tasks on physiologic parameters of individuals presently performing a set of activities throughout a shift. By studying several measures, a more accurate and reproducible assessment can be made that will allow prediction of the level of aerobic fitness required of new job entrants. The improved method does not evaluate nor address work organization or psychological issues such as how well does this job fit the intellectual abilities and interest of the individual.

Work is performed by converting potential energy into kinetic energy. The body uses food to create energy, with the volume of breath and the heart rate reflecting the amount of energy being used at any particular time. The volume of air and the heart rate can be measured in a way that enables conclusions to be drawn about specific job demands and an individual's capacity to meet those demands. To understand what we mean by energy used, one must understand the biological process. Adenosine Triphosphatase (ATP) are found in all living cells. ATP stores energy in phosphate groups. When these groups are split at their bonds, a release of energy occurs. This is true of all biological work. This energy is formed from the potential energy of food. As the energy is extracted we perform work.

Within living cells oxidation occurs when a molecule gives up an electron. Reduction occurs when a molecule accepts an electron. Stored carbohydrates, fats and proteins (food) provide hydrogen atoms. Mitochondria (energy factories) contain molecules that remove electrons from hydrogen and pass them to oxygen. During this process, high energy ATP is made. Our relative efficiency is 40% for harnessing food to create chemical energy through oxidative phosphorylation. The remaining 60% of the energy taken in as food is given off as heat.

Energy is consumed when muscles contract and relax. The more muscular effort being used, the more energy required. The key question is how does one measure the energy required for muscular contraction and relaxation to occur?. A key indicator of the amount of energy needed can be found in our cardiorespiratory system (our heart and lungs). The more energy we need, the more oxygen we need, so we breathe harder. Oxygen is carried by red blood cells, so the more oxygen we need the faster our heart beats to push the red blood cells to the muscles. If an individual's heart is efficient in squeezing out blood, that individual will get more energy from each heartbeat, and a larger volume of blood will be moved to the muscles with each beat.

One can measure the amount of air that is moved in and out of the lungs (commonly referred as ventilation) for a given period of time such as a minute. Since one knows how much oxygen is in air, typically about 21%, and assuming one has an efficient lung capacity, then knowing the amount of air used or ventilation will enable us to translate that data into a known amount of oxygen consumed under most daily work conditions. By measuring oxygen consumption, we can determine the kilocalories used by assuming a conversion factor typically 5.0 kilocalories per liter of oxygen is used. So by measuring the ventilation, and by making some calculations and adjustments, we can measure how much energy it takes to do a particular task. The more energy required doing a task the harder the work demands.

In order to get an accurate reading, one's body size (in terms of height and weight), sex and age must be taken into account. Each of these affect the resting metabolic rate. Accordingly, when practicing the method of the present invention calculations adjust for these conditions. At rest, an individual metabolic rate represents a resting oxygen use of 250 milliliters per minute for an average man, and 200 milliliters per minute for an average woman. This figure represents one MET, or multiple of the resting metabolic rate. Two METS requires 500 and 400 milliliters per minute etcetera. To translate, the liters of oxygen consumption per minute per kilogram to METS, one simply divides by 3.5. The aerobic capacity of the individual can be written either as the maximal volume of oxygen consumed per milliliter per kilogram per minute ($VO_2$ max, or as METS).

What does this mean in a work environment? For typical light work, the oxygen up take in liters per minute is up to 0.5 while the heart rate beats per minute are typically up to 90 and the energy expenditure in kilo calories per minutes is less than 2.5. For moderate work, 0.5 to 1 liters per minute of oxygen is taken in and the heart rate beats are between 90 and 110, while the energy expenditure kilo calories per minute range from 2.5 to 5.0. In heavy work the oxygen up take in liters per minute ranges from 1.0 to 1.5, the heart rate 110 to 130 and the energy expenditure 5 to 7.5 kilo calories per minute, increasing the work to very heavy workloads means that the oxygen up take ranges from 1.5 to 2 liters per minute, the heart rate beats at 130 to 150 beats per minute, while the energy consumption is 7.5 to 10 kilo calories per minute.

Since oxygen is carried by red blood cells passing through the heart, the heart rate can be used to estimate oxygen consumption and thus energy expenditure. The heart rate however, can be influenced by a variety of factors such as temperature, emotional state, the food intake, body position, and the muscle group exercised (large versus small), static or dynamic muscle use. The heart rate is a most accurate reflection when the work rate is steady. For each person there is a linear relationship between heart rate and oxygen consumption at usual rates of work. This means that if you know the heart rate at a consistent rate of work you can estimate the energy expenditure and oxygen used. Treadmills, bicycle ergonometers, and step tests are commonly used for this purpose. The more fit the individual, the lower the slope of the line, and a lower heart rate is required to offer the same amount of energy consumption. Accordingly, individuals who progressively increase their demand on the cardiorespiratory system through increasing the amount of energy expenditure will increase the stroke volume of the heart assuming no physiological reason that would preclude this from occurring like restricted heart valves or lining of the heart being damages. As a result, the output of the heart with each beat can be increased.

A typically sedentary person who is untrained will have a cardiac output at rest of 5,000 milliliters, a heart rate of 70 beats per minute and a stroke volume of 71 milliliters per beat. At maximum exercise levels this untrained individual will have 2,200 milliliters cardiac output, a heart rate of 195 beats per minute and a stroke volume of 113 milliliters per beat. A trained individual who is well fit will have an at rest cardiac output of only 500 milliliters a heart rate of only 50 beats per minute and a stroke volume of 100 milliliters per beat. This trained individual when exercised to a maximal condition will see a 35,000 milliliters cardiac output and a heart rate of 195 beats per minute with a stroke volume of 179 milliliters per beat. What this means is that the fit or trained individual will, at rest, be working his heart less than a sedentary or untrained individual while at work his volumetric output is substantially higher and therefore the amount of oxygen getting to the muscles is far superior to that of a sedentary or untrained individual.

This is important because the more oxygen you can circulate with each heartbeat the less fatigued you become at any given level for work. An individual should be working with an average of one third or less of his aerobic capacity for a shift even though you can periodically work at much higher levels. An individual knowing his or her aerobic capacity can estimate a heart rate associated with any level of energy expenditure. We know that the heart rate and oxygen efficiencies are tied and that the harder one works the higher his or her heart rate. Unfit people exhibit higher heart rates for a steady level effort than more conditioned people. Importantly, the better physical condition you are in the faster your heart rate will come down when you stop working. You will recover faster and your body will reach an at rest condition quicker than a person who is not in good physical condition.

The Process of Verification of the Energy Requirements of Jobs

Figure 7:
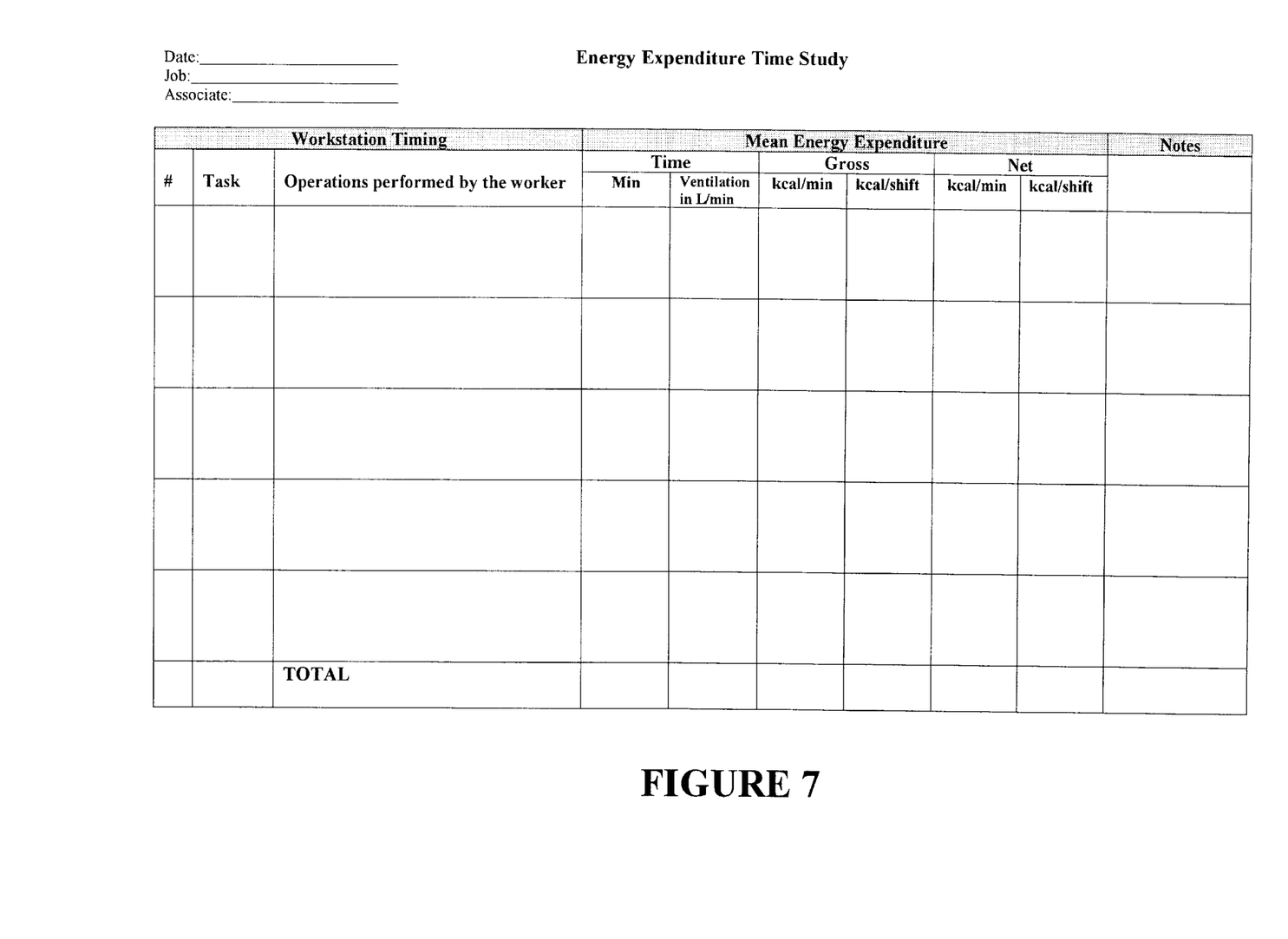
FIG. 7 is a table of activities and times activities are performed during one shift.

The physiologic information outlined above, verified by years of testing in work and sport applications, forms the basis for the invention. First, a task analysis is done to determine the pattern and timing of job components. Task requirement measurement is considered critical in that in order for certain jobs to be satisfied properly it is believed important that one should measure the jobs to know the actual requirements needed during a particular shift. As shown in FIG. 7 a typical table of activities and times required to perform those activities during one shift is documented.

Figure 1:
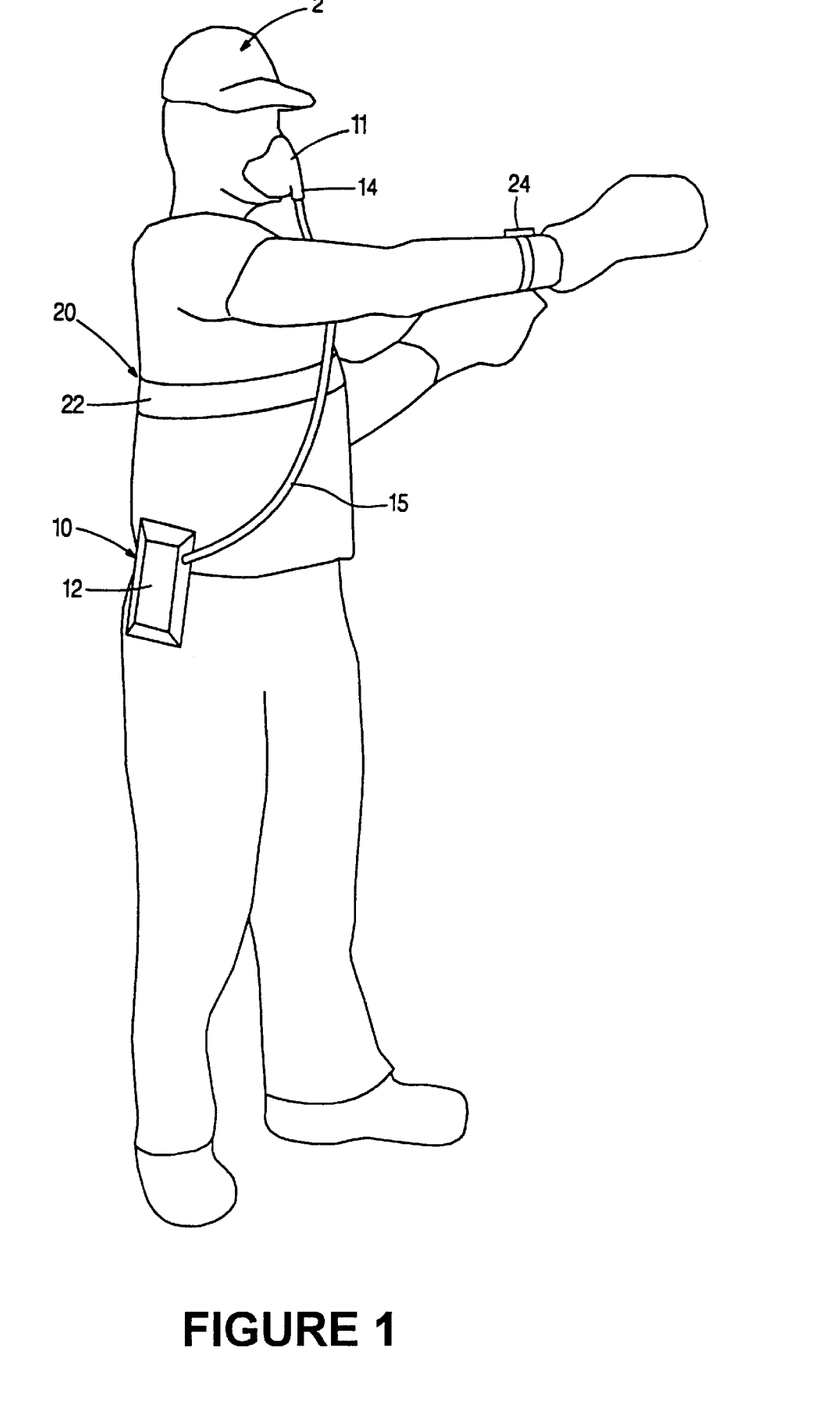
FIG. 1 is a schematic view of an individual showing the ventilation monitor and heart rate monitor attached.
Figure 6:
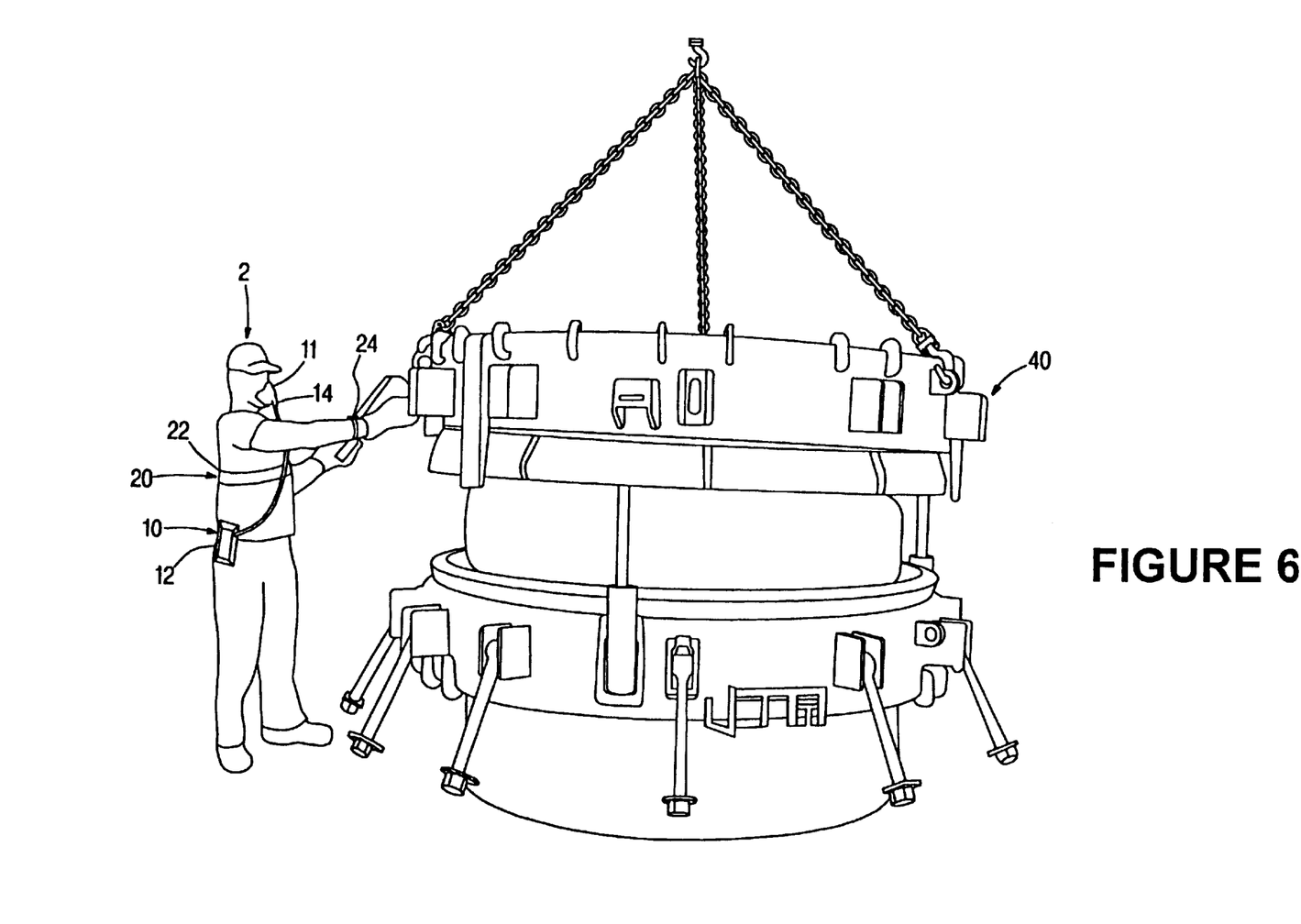
FIG. 6 is a schematic view of an individual being monitored at a job to measure task requirements.

Second, at the workstation 40, one measures the ventilation while the individual 2 wears a mask 11 having sensor 14 and a tube 15 connected to a small computer 12 which he and carries on his belt (FIGS. 1 and 6). The computer 12 calculates the energy consumption and adjusts for age, sex, height and weight. Oxygen consumption is calculated from tables, kilocalories of energy are read from the computer 12, both as gross requirements (including resting metabolic needs) and as net requirements from the work itself. Variations in the work pace by measuring the amount of time compensates for the rate in which the work is being conducted for any given activity that occurs during a shift and then adjusting for the number of those activities. A sampling of all significant tasks required has to be conducted in order to get a true measurement of the job requirements over a shift, however, this is a sampling procedure and does not require that one is monitored over an entire shift but only that the activities that are significant are monitored in such a fashion that the overall shift exposure to the work can be calculated. For the purpose of this invention, a ventilation monitor 10 called an energetic exertion meter (MWE-1) was used. The MWE-1 energetic exertion meter 10 is a portable device designed to measure human energetic exertion. This device is used in Poland and it enables classification of work to be conducted. The operation of the device or monitor is based on the measurement of lung ventilation by an airflow sensor 14. The airflow sensor 14 is inserted in a semi mask 11 and uses a small computer microprocessor unit 12 located in a separate case. This semi mask is put on the face of the examined person 2. The processing unit 12 can be hung up on a belt or other adequate part of the examined persons wardrobe using a clip. It is important to know while this device 10 measures a volume of air an individual 2 is consuming at any particular time under any level of exertion, it has valuable correlation to the amount of oxygen consumed. What makes the ventilation monitor 10 reasonably efficient is its low cost and yet its high accuracy. Most equipment currently available on the market costs tens of thousands of dollars to gather data as it relates to oxygen consumption. This device 10 on the other hand permits the measurements to be made at significantly lowered costs.

Figure 8:
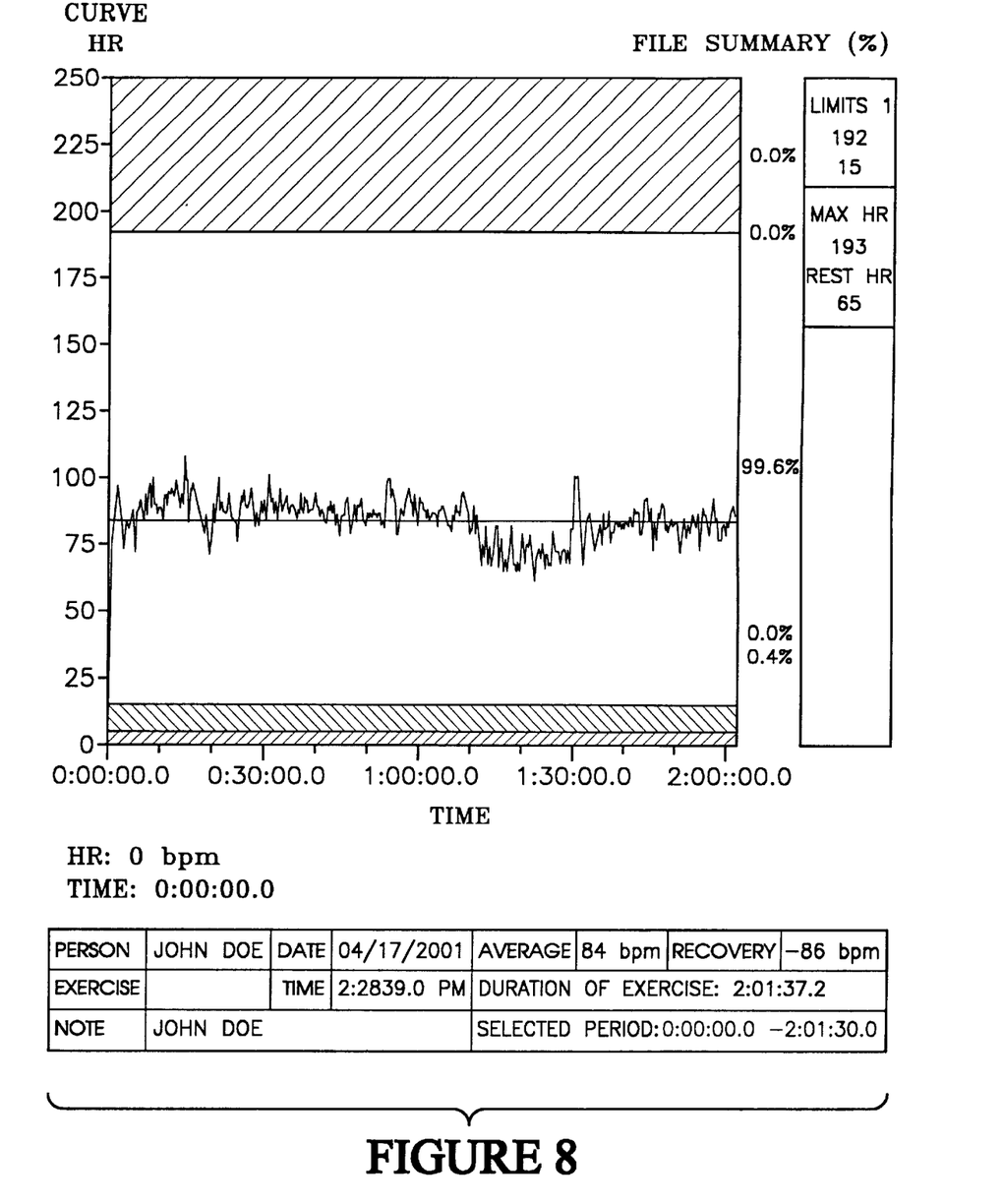
FIG. 8 is an exemplary heart rate chart.

Third, by using a heart rate monitor 20 throughout the period of the ventilation measurements, one can study the pattern during a work cycle and calculate the heart rate reserved used and the pattern of recovery. The heart rate monitor 20 as illustrated includes a chest band 22 that picks up the heart functions and wrist type device 24 for capturing the pulse rate etcetera. The information, recorded every 15 seconds during the testing period, is downloaded into a computer program for analysis. This allows both estimates of the energy required by the work and how well the individual tolerates the work rate and energy demands. The heart rate reserve equals the maximum heart rate minus the resting heart rate. The heart rate reserve utilization at any point in the work shift is equal to 100 times the heart rate at that time minus the resting heart rate divided by the age predicted maximum heart rate minus the resting heart rate. It is an objective that an individual doing continuous work exhibits less than 50% of the heart rate reserve utilization (HRRU) and less than 33% of the aerobic capacity used. His recovery heart rate at one minute should be less than 100 and at three minutes should be ten beats lower. We would expect no rise in resting heart rate during the shift as shown in the chart of FIG. 8.

Fourth, the aerobic capabilities of the individuals 2 presently performing the job are obtained. There are several established methods that can be used for the testing and each results in an estimate of the efficiency of the individual in using oxygen as compared to the heart rate response. For example, an individual who is more fit will demonstrate a lower heart rate for a given work load than an individual is less fit. This is important in the interpretation of the overall work requirements. At the time of aerobic testing, a screening protocol is used to establish the relevant baseline status of the individual 2 being tested (FIG. 5).

Fifth, the results of the oxygen consumption measurements, the working heart rate reserve utilization, and the aerobic capabilities of each individual is evaluated for consistency. If the pattern is consistent, a recommended aerobic capacity for each job entrant (2) can be established. If the patterns are not consistent, then further evaluation of the work context and individual medical presentation is required. Generally testing of one or more additional individuals, preferably at least four individual will be required. When a conclusion is reached, the aerobic capacity requirements for job entrants 2 can be established.

Figure 2:
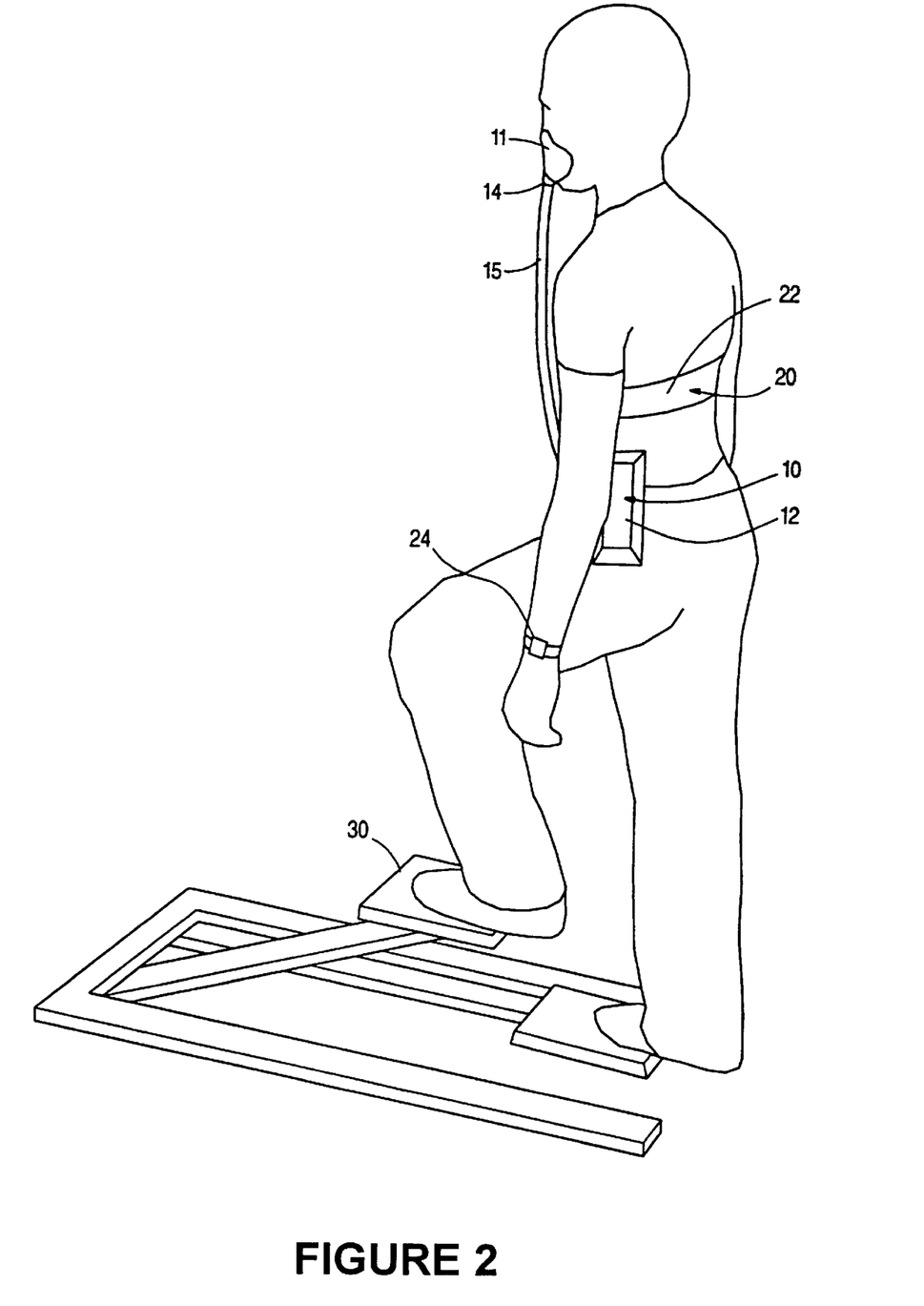
FIG. 2 is a Figure of the individual being subjected to a step test while being monitored.
Figure 3:
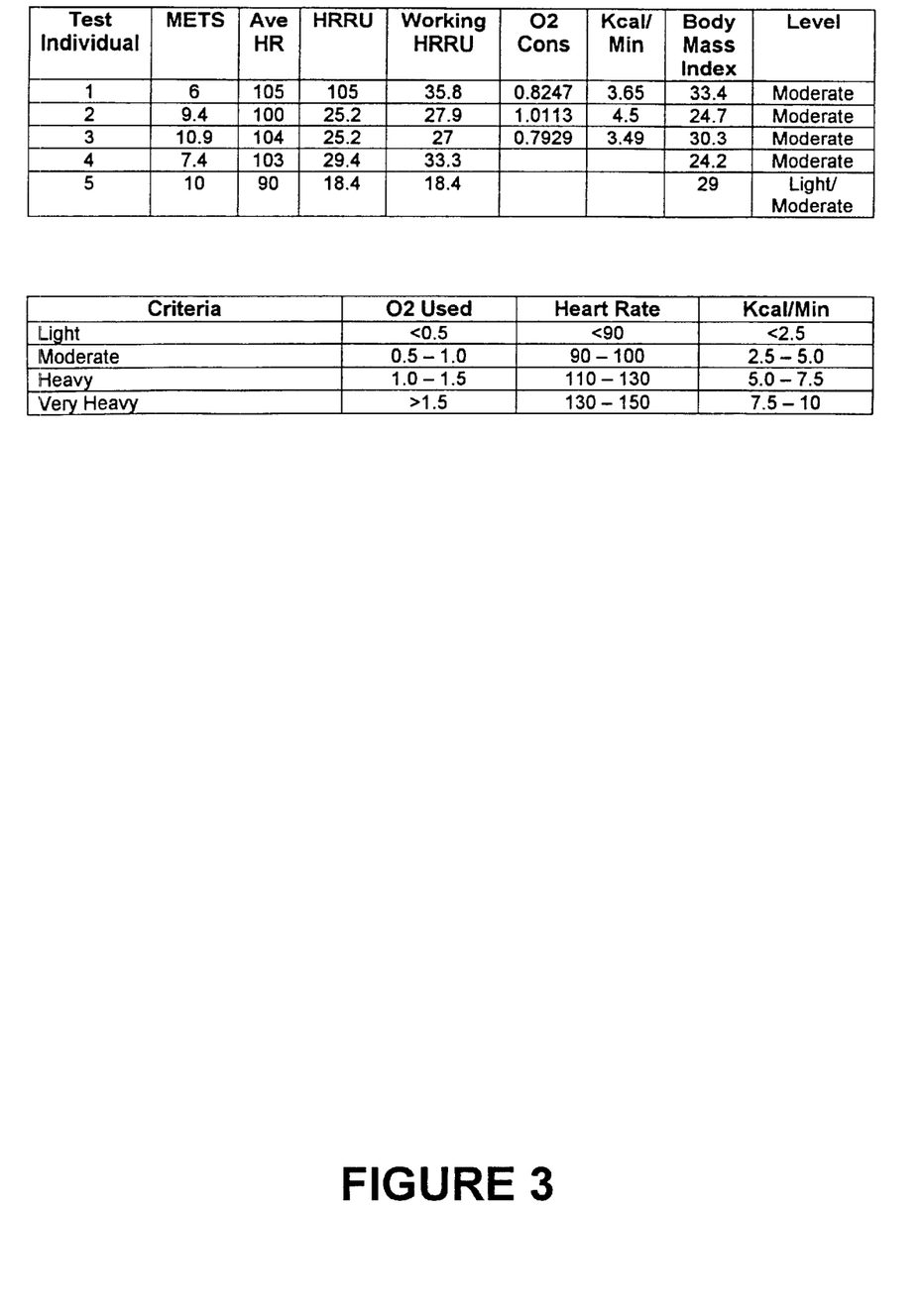
FIG. 3 is a tabular form showing the results.

As shown in FIG. 2 when testing a job entrant 2 for a job a stress test employing a step device 30 or similar equipment commonly used for such functions like a bicycle, staircase or treadmill is recommended. The individual 2 wears the ventilation monitor 10 and after a short period of time, generally 20 minutes at test condition, an entire aerobic capacity and heart rate reserve utilization determination can be calculated and filled out using the computer generated calculations. As in FIG. 3, typical results are shown for a hypothetical group of tested individuals. As shown in FIG. 4, a form entitled Aerobic Work Requirements Data Sheet is filled out providing the background history and the test results.

USE OF THE INVENTION

The process described allows for a cost effective and reliable methodology of determining the aerobic capacity required for a particular job over a particular shift. Used in conjunction with a valid method of testing for the musculoskeletal demands of the job, a comprehensive profile of physical job demands can be built. In addition, measurement of the energy consumption and the heart rate reserve utilization during the job cycle can offer a method to evaluate the need for job modification because of complaints of fatigue or excessive rates of injury.

It is appreciated that while it was known in the art that some of these elements have been done they, have not been able to be combined in such a fashion that was both cost efficient, quick and accurate. The present invention provides a unique way of achieving these results in a manner that allows large volumes of individuals to be prescreened and enumerable job functions to be analyzed in terms of aerobic requirements.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. An improved method for evaluation a work assignment or tasks by measuring the amount of energy exerted by the individuals performing the work assignment or tasks, comprising the steps of:

identifying the number of activities required by work assignment or task over the work shift; and estimate the amount of time expended at each activity;

sampling each identified activity for the rate of energy consumed; and calculating the kcal/per shift of each activity and total kcal/per shift of the task or work assignment.

2. The improved method of claim 1 further comprising the step of taking an individual having a pre tested and known aerobic capacity, attaching the individual to a heart monitor and a ventilator monitor, sampling each activity for a predetermined time;

recording the sampling results for each activity indicating the air volume intake, heart rate and rate of energy consumed per each activity; and calculating the amount of oxygen used, the work heart rate, and the energy required for the activities measured and the total work assignment or task.

3. The improved method of claim 1 further comprising:

taking one or more additional individuals having been pre tested with known aerobic capacities and repeating the steps of attaching monitors, recording data and calculating the amount of oxygen used, the work heart rate and the energy required for the activities measured and the total work assignment or task and recording the range of the calculations and the averages or mean of these calculations.

4. An improved method for evaluating an individual's capacity for performing work assignments or task, the method comprising the steps of:

identifying the individual's medical background and history;

subjecting the individual to a physical evaluation measuring the ventilation, heart rate, and aerobic capacity; wherein the measuring of ventilation capacity measures air intake volume adjusted to certain physical characteristics of the individual being tested, and the air intake volume is converted into oxygen used, the oxygen used, the average heart rate reserve utilization and the energy used are calculated, wherein the average heart rate reserve utilization must be less than 30%; and recording the evaluation results.

5. The improved method of claim 4 further comprises the steps of:

comparing the evaluation results to the work assignment or task requirements; and verifying the evaluation result meet or exceed the requirements.

6. The improved method of claim 4 wherein the individual medical background includes age, height, weight, and sex.

7. The improved method of claim 4 wherein the medical history includes any preexisting conditions or factors that could adversely influence test results.

8. The improved method of claim 7 wherein preexisting conditions or factors are compensated for or screened out prior to evaluation.

9. An improved method for evaluating an individual's capacity for performing work assignments or task, the work assignments and task each having predetermined rates of energy consumption, the method comprising the steps of:

identifying the individual's medical background and history;

subjecting the individual to a physical evaluation measuring heart rate for a work load; wherein the measuring of the heart rate is adjusted to certain physical characteristics of the individual being tested, and wherein the aerobic capacity, the heart rate reserve utilization and the energy used are calculated, wherein the acceptable average heart rate reserve utilization must be less than 30% and the acceptable aerobic capacity must be less than 33% for the physical evaluation for the work assignment; and recording the evaluation results.

* * * * *